US011583506B1

(12) United States Patent
Peñarando Sáez et al.

(10) Patent No.: US 11,583,506 B1
(45) Date of Patent: Feb. 21, 2023

(54) CANNABINOIDS FOR USE IN SUPPRESSING CANCER STEM CELLS

(71) Applicant: VIVACELL BIOTECHNOLOGY ESPAÑA S.L.U., Cordova (ES)

(72) Inventors: Jon Peñarando Sáez, Málaga (ES); Juan Diego Unciti Broceta, Cordova (ES); Eduardo Muñoz Blanco, Cordova (ES)

(73) Assignee: VIVACELL BIOTECHNOLOGY ESPAÑA S.L.U.

( * ) Notice: Subject to any disclaimer, the term of this patent is extended or adjusted under 35 U.S.C. 154(b) by 0 days.

(21) Appl. No.: 18/048,993

(22) Filed: Oct. 24, 2022

Related U.S. Application Data

(63) Continuation of application No. 17/628,415, filed as application No. PCT/ES2020/070278 on Apr. 29, 2020.

(51) Int. Cl.
*A61K 31/05* (2006.01)
*A61P 35/00* (2006.01)
*A61K 35/17* (2015.01)
*A61K 38/17* (2006.01)
*A61K 45/06* (2006.01)

(52) U.S. Cl.
CPC ............. *A61K 31/05* (2013.01); *A61K 35/17* (2013.01); *A61K 38/1774* (2013.01); *A61K 45/06* (2013.01); *A61P 35/00* (2018.01)

(58) Field of Classification Search
CPC ................................ A61K 31/05; A61P 35/00
USPC ......................................................... 514/733
See application file for complete search history.

(56) References Cited

U.S. PATENT DOCUMENTS 10,053,407 B2    8/2018    Dickman et al.

FOREIGN PATENT DOCUMENTS

| GB | 2478595 A | 9/2011 |
| GB | 2554592 A | 4/2018 |
| WO | WO 2019/222459 A1 | 11/2019 |
| WO | WO 2020/230145 A1 | 11/2020 |

OTHER PUBLICATIONS

Aster et al., The Varied Roles of Notch in Cancer. Annu Rev Pathol. Jan. 24, 2017;12:245-275.
Bocci et al., Toward understanding cancer stem cell heterogeneity in the tumor microenvironment. Proc Natl Acad Sci U S A. Jan. 2, 2019;116(1):148-157.
Chang. Cancer Stem Cells. Role in tumor growth, recurrence, metastasis, and treatment resistance. Medicine, 2016. vol. 95, No. 1 ; s20-s25.
Clarke et al., Cancer stem cells—perspectives on current status and future directions: AACR Workshop on cancer stem cells. Cancer Res. Oct. 1, 2006;66(19):9339-44.
Collura et al., Extensive characterization of sphere models established from colorectal cancer cell lines. Cell Mol Life Sci. Feb. 2013;70(4):729-42.
Dieter et al., Distinct types of tumor-initiating cells form human colon cancer tumors and metastases. Cell Stem Cell. Oct. 4, 2011;9(4):357-65.
Espinoza et al., Notch inhibitors for cancer treatment. Pharmacol Ther. Aug. 2013;139(2):95-110.
Ghajar et al., The perivascular niche regulates breast tumour dormancy. Nat Cell Biol. Jul. 2013;15(7):807-17.
Hanus et al., Phytocannabinoids: a unified critical inventory. Nat Prod Rep. Nov. 23, 2016;33(12):1357-1392.
Hinz et al., Anti-tumour actions of cannabinoids. Br J Pharmacol. May 2019;176(10):1384-1394.
Huang et al., Colorectal cancer stem cell and chemoresistant colorectal cancer cell phenotypes and increased sensitivity to Notch pathway inhibitor. Mol Med Rep. Aug. 2015;12(2):2417-24.

(Continued)

*Primary Examiner* — Raymond J Henley, III
(74) *Attorney, Agent, or Firm* — Tristan A. Fuierer; Casimir Jones SC

(57) ABSTRACT

It is disclosed a compound of formula (I), or a pharmaceutically acceptable salt or solvate thereof:

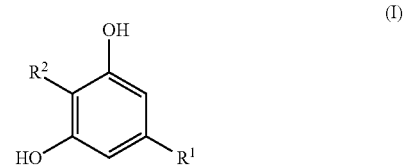

wherein $R^1$ is a linear alkyl group of 3 or 5 carbon atoms, and $R^2$ is:

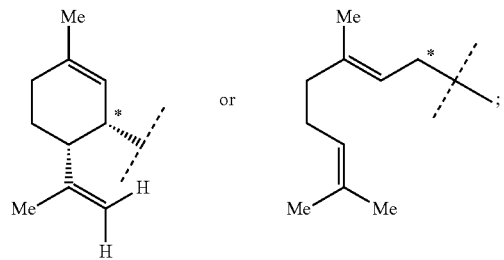

and a pharmaceutical composition comprising the same, for use in the treatment of a disease whose treatment benefits from inhibiting or reducing Notch1 expression levels in cells, and/or benefits from inhibiting or reducing Notch1 levels in cells, and/or benefits from inhibiting or reducing Notch1 signaling dependent proteins levels in cells.

As a consequence, present invention also relates to said compound of formula (I), and to the pharmaceutical composition comprising the same, for use in suppressing cancer stem cells, as well as, for use in reducing solid tumor development, metastasis or chemo/radio-resistance, promoted by cancer stem cells.

9 Claims, 8 Drawing Sheets

(56) References Cited

OTHER PUBLICATIONS

Ladin et al., Preclinical and Clinical Assessment of Cannabinoids as Anti-Cancer Agents. Front Pharmacol. Oct. 7, 2016;7:361.

Lee et al., Tumorsphere as an effective in vitro platform for screening anti-cancer stem cell drugs. Oncotarget. Jan. 12, 2016;7(2):1215-26.

Li et al., Intrinsic resistance of tumorigenic breast cancer cells to chemotherapy. J Natl Cancer Inst. May 7, 2008;100(9):672-9.

Ligresti et al., Antitumor activity of plant cannabinoids with emphasis on the effect of cannabidiol on human breast carcinoma. J Pharmacol Exp Ther. Sep. 2006;318(3):1375-87.

Meurette. Shaping of the Tumor Microenvironment by Notch Signaling. Adv Exp Med Biol. 2020;1223:1-16.

Morales et al., Antitumor Cannabinoid Chemotypes: Structural Insights. Front Pharmacol. May 31, 2019;10:621. 17 pages.

Reynolds et al., Clonal and population analyses demonstrate that an EGF-responsive mammalian embryonic CNS precursor is a stem cell. Dev Biol. Apr. 10, 1996;175(1):1-13.

Scott et al., Enhancing the activity of cannabidiol and other cannabinoids in vitro through modifications to drug combinations and treatment schedules. Anticancer Res. Oct. 2013;33(10):4373-80.

Sethi et al., Tumor-derived JAGGED1 promotes osteolytic bone metastasis of breast cancer by engaging notch signaling in bone cells. Cancer Cell. Feb. 15, 2011;19(2):192-205.

Shaheen et al., Spheroid-Formation (Colonosphere) Assay for in Vitro Assessment and Expansion of Stem Cells in Colon Cancer. Stem Cell Rev Rep. Aug. 2016;12(4):492-9.

Singh et al., Identification of a cancer stem cell in human brain tumors. Cancer Res. Sep. 15, 2003;63(18):5821-8.

Takebe et al., Targeting Notch, Hedgehog, and Wnt pathways in cancer stem cells: clinical update. Nat Rev Clin Oncol. Aug. 2015;12(8):445-64.

Toh et al., Epigenetics in cancer stem cells. Mol Cancer. Feb. 1, 2017;16(1):29.

Velasco et al., Anticancer mechanisms of cannabinoids. Curr Oncol. Mar. 2016;23(2):S23-32.

Venkatesh et al., Targeting Notch signalling pathway of cancer stem cells. Stem Cell Investig. Mar. 12, 2018; 5:5. 12 pages.

Yang et al., Targeting cancer stem cell pathways for cancer therapy. Signal Transduct Target Ther. Feb. 7, 2020;5(1):8. 35 pages.

CANNABINOIDS FOR USE IN SUPPRESSING CANCER STEM CELLS

CROSS-REFERENCE TO RELATED APPLICATIONS

This application is filed under the provisions of 35 U.S.C. § 120 and is a continuation of U.S. patent application Ser. No. 17/628,415, filed on Jan. 19, 2022, entitled "CANNABINOIDS FOR USE IN SUPPRESSING CANCER STEM CELLS" in the name of Jon PEÑARANDO SÁEZ, et al., which was filed under the provisions of 35 U.S.C. § 371 and claims the priority of International Patent Application No. PCT/ES2020/070278, filed on 29 Apr. 2020, both of which are hereby incorporated by reference herein in their entirety.

FIELD OF THE INVENTION

The present invention relates to a compound, and to a pharmaceutical composition comprising the same, for use in the treatment of a disease benefiting from Notch signaling pathway inhibition, i.e. a disease whose treatment benefits from inhibiting the Notch signaling pathway, and particularly, the Notch1 signaling pathway. As a consequence, present invention also relates to said compound, and to the pharmaceutical composition comprising the same, for use in suppressing cancer stem cells, as well as, for use in reducing solid tumor development, metastasis or chemo/radio-resistance, promoted by cancer stem cells.

BACKGROUND OF THE INVENTION

The tumor microenvironment (TME) has become a major concern of cancer research both from a basic and a therapeutic point of view. Understanding the effect of a signaling pathway and thus, the effect of its targeting by also considering every aspect of the microenvironment, is a prerequisite to predict and to analyze the effectiveness of a therapy. Different mechanisms contribute to intratumor heterogeneity, including genetic mutations, the microenvironment and the existence of subpopulations of cancer cells with increased renewal capacity which are referred hereto as cancer stem cells. In fact, cancer stem cells refer to a subpopulation of stem-like cells within tumors which exhibit characteristics of both stem cells and cancer cells.

In general, similar to normal stem cells, cancer stem cells have self-renewal and multi-directional differentiation functions, and, under certain circumstances, they will re-initiate the cell cycle to proliferate and to generate additional tumor masses that lead to tumor recurrence. Therefore, the presence of cancer stem cells has been identified as an important cause of tumor recurrence and metastasis. At present, there is still a lack of specific antitumor drugs for cancer stem cells, and research on drugs targeting cancer stem cells is necessary.

During clinical treatment, the cancer stem cells that contribute to recurrent tumors are highly resistant to traditional antitumor drugs, which causes serious interference for subsequent treatment. Cancer therapy is primarily hindered by recurrence and chemo/radio-resistance (i.e., tumors not responding or resistant to chemotherapy and/or radiotherapy). Accumulating evidence has suggested that cancer stem cells, which initiate and maintain tumor growth, are a small subset of tumor cells. Cancer stem cells are thought to cause tumor relapse, metastasis and chemo/radio-resistance, and have been identified in many types of solid tumors, including pancreatic, breast, lung and liver tumors.

Traditional chemotherapy eliminates the bulk of tumor cells but cannot eradicate cancer stem cells, which have enhanced cell repair and cell renewal abilities (Clarke M F et al. Cancer Res. 2006 Oct. 1; 66(19):9339-44. PMID: 16990346). Due to their self-renewal ability and therapy resistance, cancer stem cells are considered the root cause of tumorigenesis, progression, drug resistance and recurrence (Chang J C et al. Cancer stem cells: Role in tumor growth, recurrence, metastasis, and treatment resistance. Medicine (Baltimore). 2016 September; 95(1 Suppl 1): S20-5. doi: 10.1097/MD.0000000000004766. PMID: 27611935). Previous studies have found that cancer stem cells are enriched after chemotherapy (Li X et al. J Natl Cancer Inst. 2008 May 7; 100(9):672-9. doi: 10.1093/jnci/djnl23. PMID: 18445819). Multiple signaling pathways are abnormally activated in cancer stem cells and, therefore, targeting cancer stem cells is a more effective approach for treating cancer. Evidence have shown that abnormalities in different signaling pathways exist in cancer stem cells, including the Notch, Hedgehog (Hh), and Wnt pathways, which play vital roles in embryonic development and differentiation of normal stem cells. In addition, the TME releases cytokines that increase activation of these signaling pathways to enhance the cancer stem cell population (Bocci F et al. Proc Natl Acad Sci USA. 2019 Jan. 2; 116(1):148-157. doi: 10.1073/pnas.1815345116. PMID: 30587589).

Cannabis has long been known to limit or prevent nausea and vomiting, lack of appetite, and pain. For this reason, cannabinoids have been successfully used in the treatment of some of the unwanted side effects caused by cancer chemotherapy. Besides their palliative effects, research from the past two decades has demonstrated their promising potential as antitumor agents in a wide variety of tumors. Therefore, in addition to such palliative applications, some cannabinoids have also shown anticancer properties.

As widely reported in the last decades, some cannabinoids are able to modulate different cellular signaling pathways implicated in cancer cell proliferation, migration, or death. Even though the underlying mechanisms are not totally unrevealed, there is significant evidence for the involvement of at least four mechanisms: direct inhibition of transformed-cell growth through the suppression of mitogenic signal, induction of apoptosis, inhibition of tumor angiogenesis and inhibition of metastasis for, at least, some cannabinoids (Velasco G et al. Curr Oncol. 2016. 23(2): S23-32. doi: 10.3747/co.23.3080. PMID: 27022311). So far, only few clinical data on the efficacy of cannabinoids as anticancer agents have been provided (Ladin D A et al. Front Pharmacol. 2016; 7:361. doi: 10.3389/fphar.2016.00361. PMID: 27774065).

The plant-derived family of cannabinoids is exemplified by the phytocannabinoids: tetrahydrocannabinol (−)-$\Delta^9$-THC), cannabidiol (−)-CBD and cannabigerol (−)-CBG the three main components of *Cannabis sativa*. Varin cannabinoids as cannabigerivarin (CBGV), tetahydrocannabivarin ($\Delta^9$-THCV), or cannabidivarin (CBDV), are derived from the corresponding varin acids: cannabigerovarinic acid (CBGV-A), tetrahydrocannabivarinic acid (THCV-A), or cannabidivarinic acid (CBDV-A). Cannabinoids have side-chains made up of five carbon atoms, whereas varin cannabinoids have side-chains made up of three carbon atoms (Hanuš L O et al. Nat Prod Rep. 2016; 33(12):1357-1392. PMID: 27722705).

Reports on anticancer effects of phytocannabinoids mainly have been focused on the activity of $\Delta^9$-THC, CBD, Δ⁹-tetrahydrocannabinolic acid (Δ⁹-THCA), cannabidiolic acid (CBDA), CBG, and cannabichromene (CBC) (Morales P et al. Front Pharmacol. 2019. 10:621. doi: 10.3389/fphar.2019.00621. PMID: 31214034). Also, cannabigerovarin (CBGV) has been studied in vitro for its anti-leukemic activity but not in solid tumors (Scott K A et al. Anticancer Res. 2013 33(10):4373-80. PMID: 24123005). The anticancer effects of Δ⁹-THC have been tested in different cell lines of prostate cancer, breast cancer, colon cancer, pancreatic cancer, lymphoma, lung cancer, glioblastoma, and myeloma, among others. Intracellular signaling through CBR has been shown to play an important role in these anticancer effects, involving complex signal transduction pathways through the ceramide pathway and/or the P13-K and ERK pathways. The non-psychoactive cannabinoid CBD revealed proapoptotic effects in different cancer cell lines and several molecular targets have been suggested as responsible of those proapoptotic effects, such as the COX-2, 5-LOX, PPARγ, mTOR, and p38 MAPK pathway (Hinz B et al. Br J Pharmacol. 2019; 176(10):1384-1394. doi: 10.1111/bph.14426. PMID: 30019449). On the other hand, Δ⁹-THCV and CBDV are being assessed for the treatment of glucose intolerance in diabetic patients and in adult epilepsy, respectively.

However, none of those treatments are linked to cancer stem cells nor have been proven useful in reducing the causes of tumor recurrence, chemo/radio-resistance and metastasis. Since cancer stem cells are precisely linked to tumor relapse, metastasis, and chemo/radio-resistance, there is currently the need to develop novel therapies to suppress cancer stem cells, including both cancer stem cell self-renewal, as well as cancer stem cell proliferation and accordingly, to develop novel therapies that suppress tumor development, metastasis and chemo/radio-resistance specifically promoted by cancer stem cells.

BRIEF DESCRIPTION OF THE INVENTION

Present invention refers to a compound of formula (I):

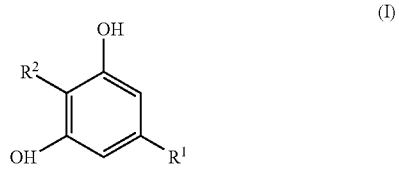

wherein $R^1$ is a linear alkyl group of 3 or 5 carbon atoms, and $R^2$ is:

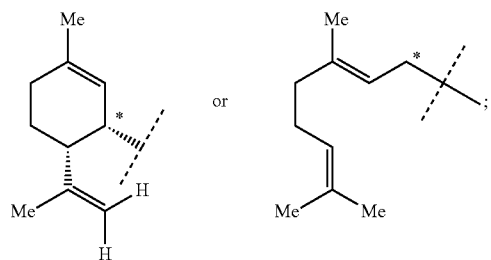

or to a pharmaceutical composition comprising the same, for use in suppressing cancer stem cells.

For the purposes of present specification, the discontinuous line "------" truncating or cutting through a bond of the $R^2$ groups of the compounds of formula (I) indicates the place of union between the atom marked with an * and the carbon of the benzene ring to which said $R^2$ group is attached.

Also, for the purposes of present specification the bonds marked with a wavy line refer to bonds which may in one of the two possible stereochemical configurations, and thus, according to present invention, a bond marked with a wavy line comprises each of said two stereochemical configurations.

Present invention also relates to the above referred compound of formula (I), or to a pharmaceutical composition comprising the same, for use in reducing solid tumor development, metastasis or chemo/radio-resistance, promoted by cancer stem cells.

Additionally, present invention relates to the above referred compounds of formula (I), or to a pharmaceutical composition comprising the same, for use in the treatment of a disease benefiting from Notch signaling pathway inhibition, i.e., a disease whose treatment benefits from inhibiting the Notch signaling pathway, and particularly, the Notch1 signaling pathway. More specifically, present invention discloses compounds of formula (I) for use in the treatment of a disease whose treatment benefits from inhibiting or reducing Notch1 expression levels in cells, and/or benefits from inhibiting or reducing Notch1 levels in cells, and/or benefits from inhibiting or reducing Notch1 signaling dependent proteins levels in cells.

FIG. 5. The compounds of formula (I), CBD, CBDV and CBGV, reduce Notch1 expression levels in HCT 116 cells: Notch1 expression levels in HCT 116 cells after 24 hours of treatment with vehicle (DMSO) or 10 µM of the following natural cannabinoids: (SA) CBD, CBDA, CBDV, CBC, CBCA, CBCV, CBG, and (SB) CBD, CBGA, CBGV, CBGVA, CBN, THC and THCA. Actin was used as control. Bar graphs (SC) and (SD) represent the quantification of Notch1 expression levels by densitometry analysis of the indicated compounds. Densitometry analysis was performed using ImageJ software, and band intensities were normalized with regard to Actin.

Figure 6A:
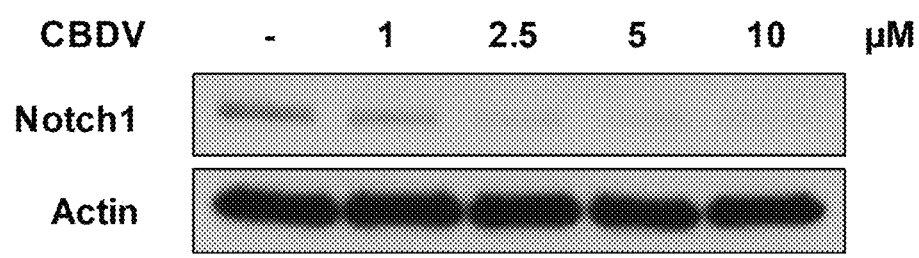
Figure 6B:
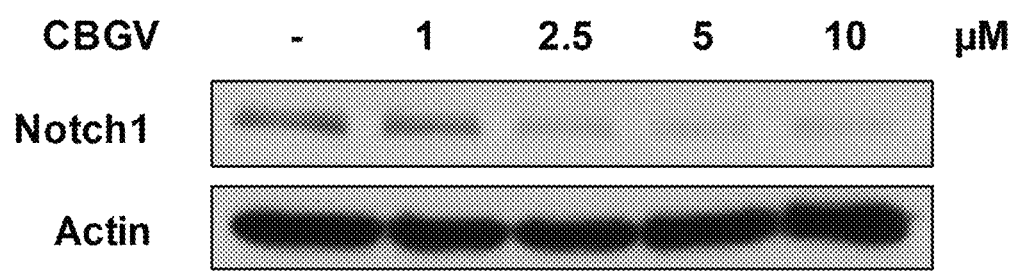

FIG. 6. The compounds of formula (I), CBDV and CBGV, reduce Notch1 expression levels in a concentration-dependent manner in HCT 116 cells: (6A) Notch1 expression levels in HCT 116 cells after 24 hours of treatment with vehicle (DMSO) or with CBDV (1, 2.5, 5 and 10 µM). (6B) Notch1 expression levels in HCT 116 cells after 24 hours of treatment with vehicle (DMSO) or with CBGV (1, 2.5, 5 and 10 µM). Actin was used as control.

Figure 7A:
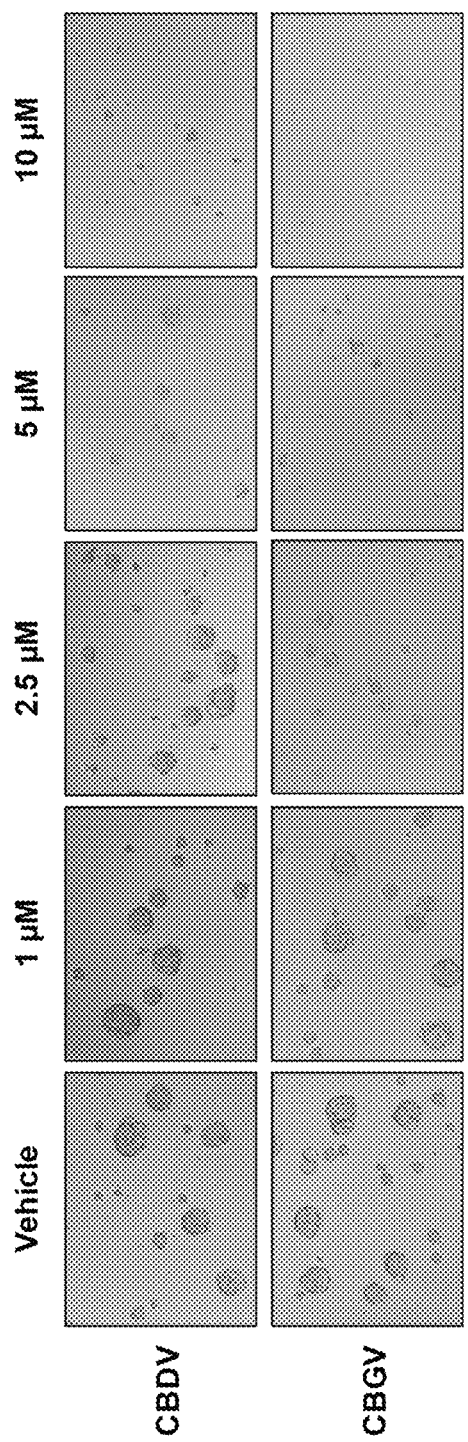
Figure 7B:
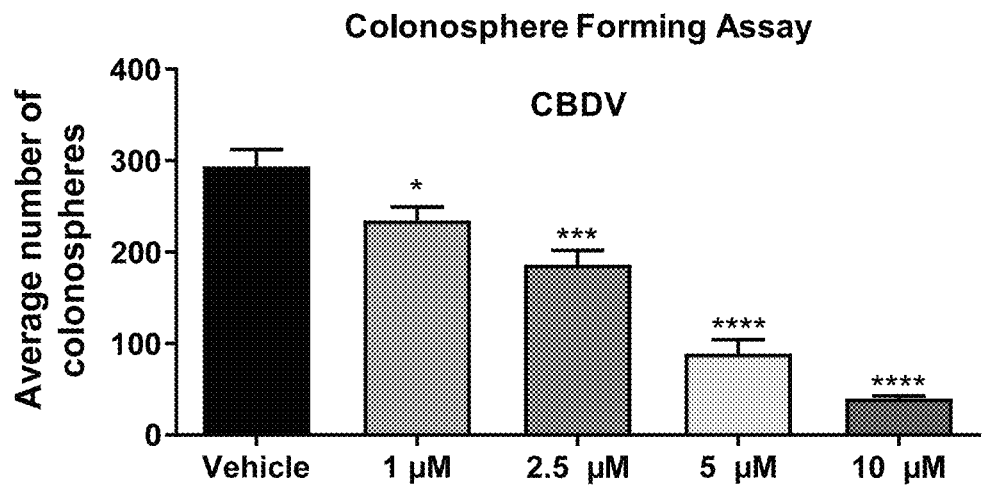
Figure 7C:
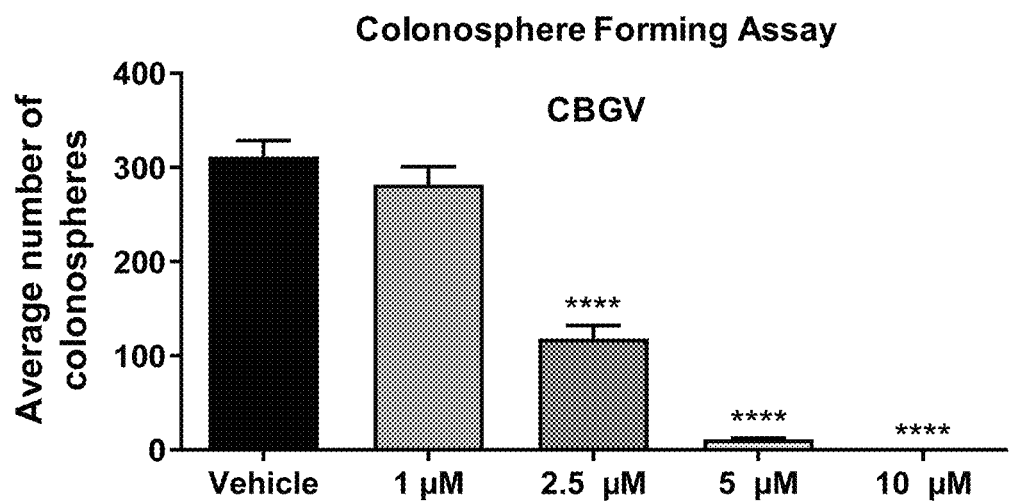

FIG. 7. The compounds of formula (I), CBDV and CBGV, inhibit colonospheres formation. (7A) Representative images of colonospheres formed by HCT 116 cells after 7 days of treatment with vehicle (DMSO) or with CBDV or CBGV (1, 2.5, 5 and 10 µM). (7B) Bar graph of the number of colonospheres formed by HCT-116 cells after 7 days of treatment with vehicle (DMSO) with CBDV or (7C) with CBGV (1, 2.5, 5 and 10 µM). Data are represented as mean f SEM (n=4, fields of views per condition). Statistical significance was determined by one-way ANOVA followed by Dunnett's post-hoc test. *p<0.05; *p<0.001; **p<0.0001 vs vehicle control cells.

DETAILED DESCRIPTION OF THE INVENTION

Present invention refers to a compound of formula (I), or a pharmaceutically acceptable salt or solvate thereof:

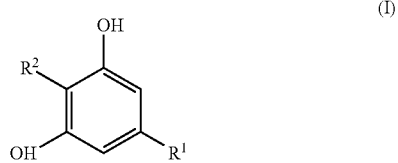

(I)

wherein $R^1$ is a linear alkyl group of 3 or 5 carbon atoms, and $R^2$ is:

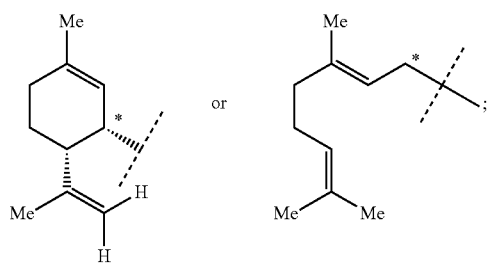

for use in the treatment of a disease benefiting from inhibiting the Notch signaling pathway. In this sense, and for the purposes of present invention, said disease is therefore, a disease whose treatment benefits from inhibiting the Notch signaling pathway, and in particular the Notch1 signaling pathway. More specifically, present invention discloses compounds of formula (I) for use in the treatment of a disease whose treatment benefits from inhibiting or reducing Notch1 expression levels in cells, and/or benefits from inhibiting or reducing Notch1 levels in cells, and/or benefits from inhibiting or reducing Notch1 signaling dependent proteins levels in cells. Preferably the Notch1 signaling dependent proteins are the transcription factors Hes1 and Hes5. Recent studies have shown that Hes1 and Hes5 play an important role in the maintenance of cancer stem cells (CSCs), metastasis and antagonizing drug-induced apoptosis (Toh, T. B. et al., Mol Cancer 16, 29 (2017), doi:10.1186/s12943-017-0596-9).

In fact, the compounds of formula (I) for use according to present invention provide an inhibitory effect on Notch1 expression levels in cells, result into the reduction of Notch1 levels in cells, and Notch1 signaling dependent proteins levels in cells, such as Hes1, and induce Notch1 degradation, as shown in the examples of present invention.

The Notch signaling pathway is involved in every component of the tumor microenvironment including cancer stem cells, as well as in the interaction between the different parts of the tumor microenvironment. Notch pathway is a juxtacrine signaling pathway that mediates cell fate decision between neighbor cells.

The implication of Notch signaling has been described in cancers (Aster J C et al. Annu Rev Pathol. 2017. 12:245-275. doi: 10.1146/annurev-pathol-052016-100127. PMID: 27959635). In fact, Notch signaling is aberrantly activated in different solid tumors. Furthermore, Notch ligands and receptors are widely expressed in the different compartments of the tumor microenvironment (TME) (Meurette O, Adv Exp Med Biol. 2020; 1223:1-16. doi: 10.1007/978-3-030-35582-1_1. PMID: 32030682). Occurrence of heterotypic activation between distinct cell populations is thus likely. For example, in small cell lung cancers, Notch signaling maintains heterogeneity between different populations of tumor cells and has been described to regulate angiogenesis, activation of fibroblasts, maintenance of the stem cell niche, the immune infiltrate and may also regulate physical and chemical heterogeneity of TME.

Establishment by cancer cell of a favorable environment is crucial for the spreading of the disease and colonization of metastatic sites. The role of Notch signaling is here also of major importance in different metastatic situations. Concerning the bone metastatic niche, cancer cell-derived Jag1 induces osteoclast differentiation through Notch activation in osteoblasts (Sethi N et al. Cancer Cell. 2011; 19(2):192-205. doi: 10.1016/j.ccr.2010.12.022. PMID: 21295524). Interaction with tenascin-C is also important in the establishment of lung metastasis by breast cancer cells through activation of Notch signaling in the metastatic niche. In brain metastasis, breast cancer cell secretion of IL-1β induces Jag1 expression in astrocytes, which then activates Notch signaling in cancer cells. By regulating the tip/stalk ratio, Notch is also implicated in regulating the escape of metastasizing cancer cells from dormancy, as tip cells are associated with this process (Ghajar C M et al. Nat Cell Biol. 2013; 15(7):807-17. doi: 10.1038/ncb2767. PMID: 23728425). Notch is therefore not only involved in shaping the TME of the primary cancer site but also participated in the establishment of a favorable environment for metastatic spreading.

Many in vitro and in vivo studies showed the effect of Notch inhibition on cancer cell proliferation, migration, and reducing stem cell phenotype. Regarding the effects on the TME, the best characterized effect of inhibiting Notch signaling on the TME is the effect on the tumor vasculature (Meurette O. Adv Exp Med Biol. 2020; 1223:1-16. doi: 10.1007/978-3-030-35582-1_1. PMID: 32030682).

In this sense, another aspect of present invention relates to a compound of formula (I), or a pharmaceutically acceptable salt or solvate thereof:

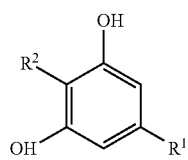
(I)

wherein $R^1$ is a linear alkyl group of 3 or 5 carbon atoms, and $R^2$ is:

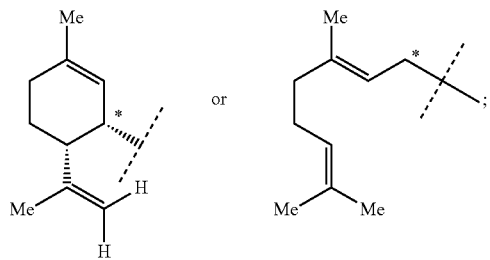

for use in reducing solid tumor development, metastasis and chemo/radio-resistance, promoted by cancer stem cells.

On the other hand, as it is the case for stem cells in normal tissues, the cancer stem cells are localized in specific niches and the role of different signaling pathways including Notch signaling in cancer stem cell maintenance has been well described (Takebe N et al. Nat Rev Clin Oncol. 2015 August; 12(8):445-64. doi:10.1038/nrclinonc.2015.61. PMID: 25850553). As seen in example 1, the compounds of formula (I) are also useful to suppress or impede the formation of cancer stem cells.

Accordingly, present invention also relates to the above referred compound of formula (I), or a pharmaceutically acceptable salt or solvate thereof:

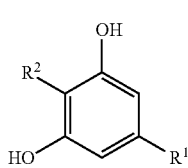
(I)

wherein $R^1$ is a linear alkyl group of 3 or 5 carbon atoms, and $R^2$ is

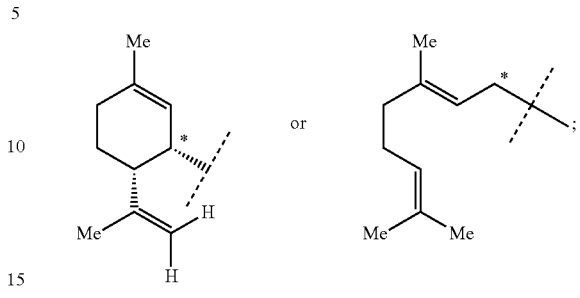

for use in suppressing cancer stem cells.

The compounds of formula (I) may be used, accordingly, in any cancer where cancer stem cells may appear, providing a useful therapeutic approach. Preferably, the cancer is a solid tumor. Also preferably, the cancer is selected from the group consisting of: colon cancer, colorectal carcinoma, colorectal adenocarcinoma, prostate cancer, prostate adenocarcinoma, prostate carcinoma, breast cancer, breast carcinoma, breast adenocarcinoma, triple negative breast cancer, brain cancer, brain adenocarcinoma, brain neuroblastoma, lung cancer, lung adenocarcinoma, lung carcinoma, small cell lung cancer, ovarian cancer, ovarian carcinoma, ovarian adenocarcinoma, uterus cancer, gastroesophageal cancer, renal cell carcinoma, clear cell renal cell carcinoma, endometrial carcinoma, endometrial stromal sarcoma, carcinoma of the uterine cervix, thyroid carcinoma, metastasizing papillary thyroid carcinoma, follicular thyroid carcinoma, bladder carcinoma, urine bladder carcinoma, transitional cell carcinoma of the urinary bladder, liver cancer, liver metastatic cancer, pancreatic cancer, neuroendocrine cancers, squamous cell carcinoma, osteosarcoma, rhabdomyosarcoma, embryonal cancers, glioma, neuroblastoma, medulloblastoma, retinoblastoma, nephroblastoma, hepatoblastoma, melanoma, hematological malignancies such as leukemias, lymphomas and myelomas; etc. In a further preferred embodiment, the cancer is a metastatic cancer or a chemo/radio-resistant tumor.

For the purposes of present invention, the term "chemo/radio-resistant tumor" or "chemo/radio-resistant cancer" refers to a cancer condition where a chemotherapeutic treatment, or radiotherapy, has not provided a remission of said cancer or tumor.

In a preferred embodiment, when $R^1$ is a linear alkyl group of 3 carbon atoms, $R^2$ is:

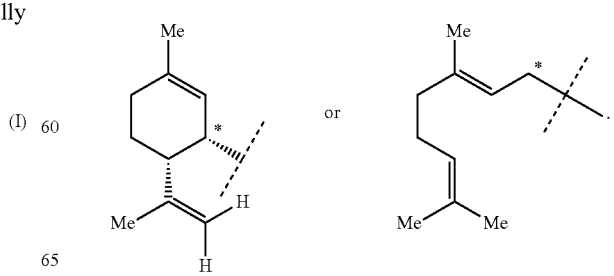

In another preferred embodiment, when $R^1$ is a linear alkyl group of 5 carbon atoms, $R^2$ is

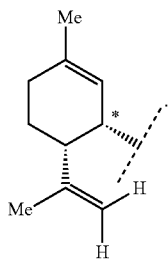

In a more preferred embodiment, the compound of formula (I) for use according to present invention is cannabidiol (CBD), cannabidivarin (CBDV) or cannabigerovarin (CBGV), or a stereoisomer, or a mixture of stereoisomers thereof:

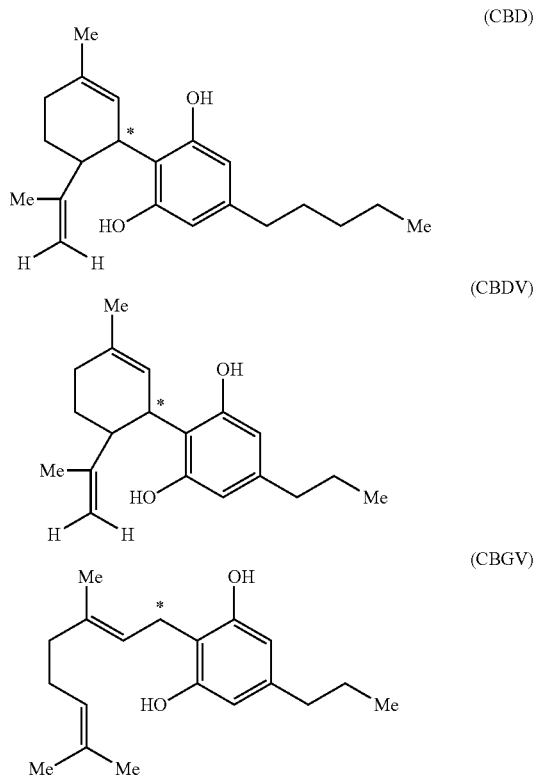

The term "isomer" is defined formally by the IUPAC (International Union of Pure and Applied Chemistry) as one of several species (or molecular entities) that have the same atomic composition (molecular formula) but different formulae or different stereochemical formulae. According to present invention the term "isomer" includes stereoisomers and conformational isomers. The term "conformational isomer" refers to those compounds which have the same molecular formula but have their atoms bonded together in different manners. On the other hand, the term "stereoisomers" is defined formally by the IUPAC as compounds, which have identical chemical constitution, but differ with regard to the arrangement or orientation of the atoms or groups in space, and are not superimposable, including, thus also, cis-trans stereoisomers (also referred as E/Z stereoisomers), and R/S stereoisomers. Since rotation is not possible on double bonds, cis-trans stereoisomers refer to the two possible configurations of the substituents of said double bond. On the other hand, R/S stereoisomers refer to compounds having at least one asymmetric or chiral carbon (having all four different substitutions). The term R or S is a formal definition accounting for the order of the different substitutions of the chiral carbon. For each chiral carbon two possible configurations R/S are possible and therefore, the total number of stereoisomers is $2^n$, where n is the number of chiral carbons. Among those stereoisomers, enantiomers are a pair of stereoisomers which are mirror images, non-superimposable, and have opposite arrangement of the substituents of all their chiral carbons. Enantiomers have different ability to rotate plane-polarized light in different directions. Due to these optical properties, the enantiomers are named (−) and (+) due to their ability to rotate plane-polarized light respectively to the left (levorotation) or to the right (dextrorotation). When a molecule has more than one chiral carbon (for example 2 chiral carbons), it includes the same number of pairs of enantiomers as the number of chiral carbons. For example a molecule having two chiral carbons includes thus 2 pairs of enantiomers having the opposite chiral configuration for each of its chiral carbons: one pair formed by molecules RR (both chiral carbons with R configuration) and SS (both chiral carbons with S configuration) and a second pair formed by molecules RS and SR. However, the stereoisomers having the same configuration R/S on some, but not all, of said chiral atoms are called diastereomers. For instance, when two chiral carbons are present, $2^2=4$ stereoisomers are possible (RR, SS, RS and SR), among which, for example, molecules RR and RS are diastereomers, whereas RR and SS, or RS and SR are enantiomers.

In this regard, the compound of formula (I) for use according to present invention includes also their possible isomers. In particular, when the compound of formula (I) is cannabidiol (CBD), the compound for use according to present invention also refers to any of the isomers thereof. In this sense, when referred to CBD, the compound of formula (I) comprises 7 double bond isomers (conformational isomers), corresponding to the position of the double bond in the cyclohexene moiety, as well as all the optical stereoisomers (enantiomers and diastereomers) for each of said conformational isomers, resulting from the chiral carbon(s) included in said double bond isomers.

In a preferred embodiment the compound of formula (I) for use according to present invention is naturally occurring CBD:

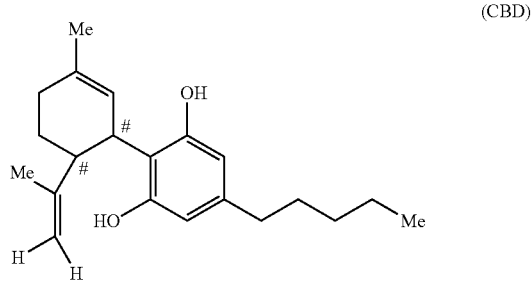

or an enantiomer or diastereomer thereof.

In more preferred embodiment, the compound of formula (I) for use according to present invention is (−)-cannabidiol, also referred as (−)-CBD, or (+)-cannabidiol, also referred as (+)-CBD, or mixtures thereof:

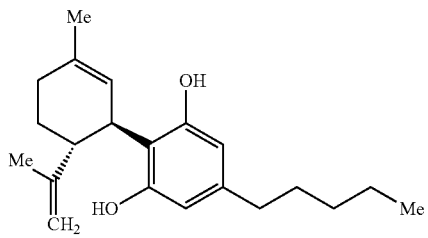

(−)-CBD

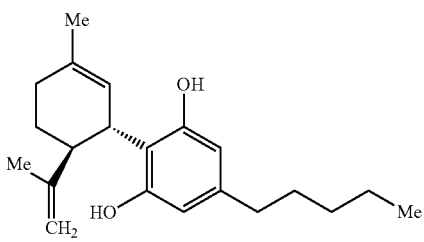

(+)-CBD

More preferably, the compound of formula (I) for use according to present invention is (−)-cannabidiol:

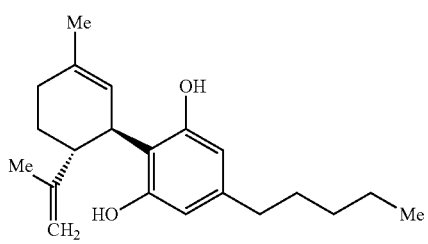

(−)-CBD

Additionally, when the compound of formula (I) is cannabidiol (CBDV), the compound for use according to present invention also refers to any of the isomers thereof. In this sense, when referred to CBDV, the compound of formula (I) comprises 7 double bond isomers (conformational isomers), corresponding to the position of the double bond in the cyclohexene moiety, as well as all the optical stereoisomers (enantiomers and diastereomers) for each of said conformational isomers, resulting from the chiral carbon(s) included in said double bond isomers.

In a preferred embodiment the compound of formula (I) for use according to present invention is naturally occurring CBDV:

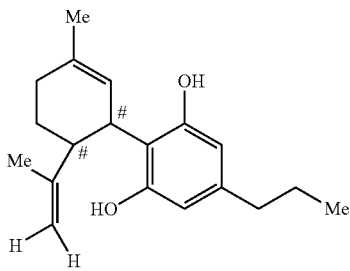

CBDV or an enantiomer or diastereomer thereof.

In more preferred embodiment, the compound of formula (I) for use according to present invention is (−)-cannabidivarin, also referred as (−)-CBDV, and (+)-cannabidivarin, also referred as (+)-CBDV:

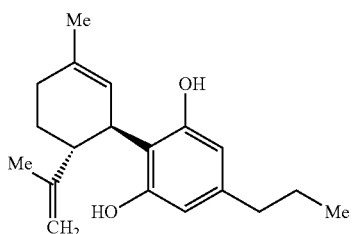

(−)-CDBV

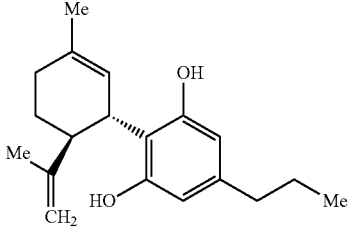

(+)-CDBV

Finally, when the compound of formula (I) is cannabigerovarin (CBGV):

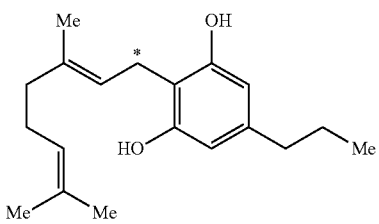

CBGV the compound for use according to present invention also refers to any of the cis- and trans-stereoisomers thereof, in relation to the double bonds included in the prenylated group $R^2$. In this regard, when the compound of formula (I) is CBGV, the double bonds of group $R^2$ may be in configuration cis-cis, cis-trans, trans-cis or trans-trans, or include a mixture of said stereoisomers.

As previously mentioned, the compound for use according to present invention is a compound of formula (I), or a pharmaceutically acceptable salt or solvate thereof.

The term "pharmaceutically acceptable salt" refers to any pharmaceutically acceptable salt, which upon administration to the patient is capable of providing (directly or indirectly) a compound as described herein. Such salts preferably are acid addition salts with physiologically acceptable organic or inorganic acids, or alkali addition salts with physiologically acceptable organic or inorganic bases. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkyleneethanolamine, triethanolamine and basic aminoacids salts. However, it will be appreciated that non-pharmaceutically acceptable salts also fall within the scope of the invention since those may be useful in the preparation of pharmaceutically acceptable salts. Procedures for salt formation are conventional in the art.

The term "solvate" in accordance with this invention should be understood as meaning any form of the active compound in accordance with the invention in which said compound is bonded by a non-covalent bond to another molecule (normally a polar solvent), including especially hydrates and alcoholates.

Present invention also refers to a pharmaceutical composition comprising at least one compound of formula (I), or a pharmaceutically acceptable salt or solvate thereof:

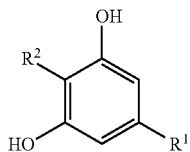
(I)

wherein $R^1$ is a linear alkyl group of 3 or 5 carbon atoms, and $R^2$ is

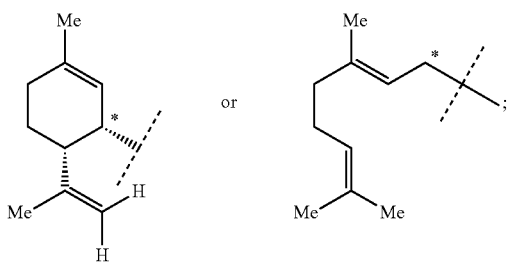

and at least one pharmaceutically acceptable excipient, for use in suppressing cancer stem cells.

Additionally, present invention also refers to a pharmaceutical composition comprising at least one compound of formula (I), or a pharmaceutically acceptable salt, or solvate thereof:

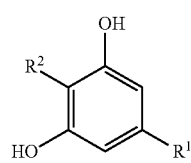
(I)

wherein $R^1$ is a linear alkyl group of 3 or 5 carbon atoms, and $R^2$ is:

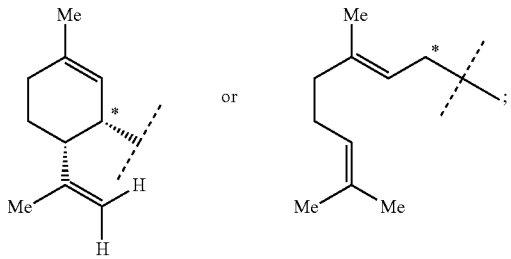

and at least one pharmaceutically acceptable excipient, for use in reducing solid tumor development, metastasis or chemo/radio-resistance, promoted by cancer stem cells.

Finally, present invention refers to a pharmaceutical composition comprising at least one compound of formula (I), or a pharmaceutically acceptable salt, or solvate thereof:

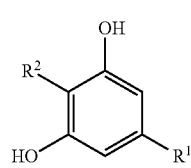
(I)

wherein $R^1$ is a linear alkyl group of 3 or 5 carbon atoms, and $R^2$ is

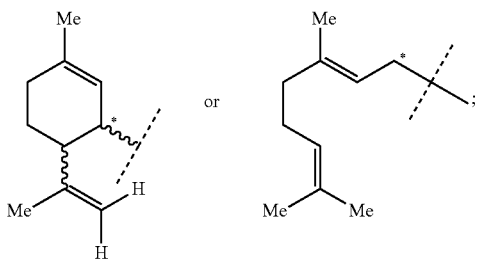

and at least one pharmaceutically acceptable excipient, for use in the treatment of a disease benefiting from Notch signaling pathway inhibition, i.e., a disease whose treatment benefits from inhibiting the Notch signaling pathway, and particularly, the Notch1 signaling pathway. More specifically, present invention discloses pharmaceutical compositions comprising compounds of formula (I), for use in the treatment of a disease whose treatment benefits from inhibiting or reducing Notch1 expression levels in cells, and/or benefits from inhibiting or reducing Notch1 levels in cells, and/or benefits from inhibiting or reducing Notch1 signaling dependent proteins levels in cells. Preferably said Notch1 signaling dependent proteins are transcription factors Hes1 and Hes5.

One embodiment refers as well to the use of a compound of formula (I), or a pharmaceutically acceptable salt or solvate thereof:

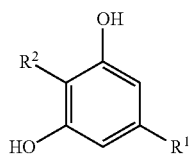
(I)

wherein $R^1$ is a linear alkyl group of 3 or 5 carbon atoms, and $R^2$ is:

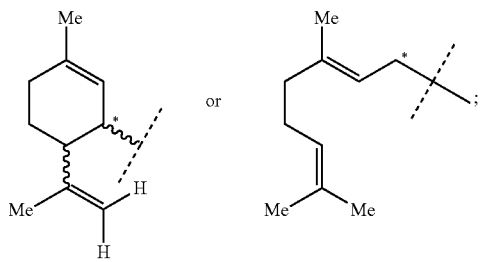

or of a pharmaceutical composition comprising the same, in the manufacturing of a medicament for suppressing cancer stem cells; or of a medicament for reducing solid tumor development, metastasis or chemo/radio-resistance, promoted by cancer stem cells; or of a medicament for the treatment of a disease benefiting from inhibiting the Notch signaling pathway, i.e., a disease whose treatment benefits from inhibiting the Notch signaling pathway, and particularly, the Notch1 signaling pathway. More specifically, present invention discloses the manufacturing of medicaments comprising as active principle compounds of formula (I), for the treatment of a disease benefiting from inhibiting the Notch signaling pathway, i.e. a disease whose treatment benefits from inhibiting or reducing Notch1 expression levels in cells, and/or benefits from inhibiting or reducing Notch1 levels in cells, and/or benefits from inhibiting or reducing Notch1 signaling dependent proteins levels in cells. Preferably, said Notch1 signaling dependent proteins are transcription factors Hes1 and Hes5.

Another embodiment refers to a method for suppressing cancer stem cells in a subject in need thereof, wherein said method comprises administering to said subject an effective amount of a compound of formula (I), or a pharmaceutically acceptable salt or solvate thereof:

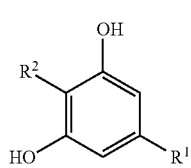
(I)

wherein $R^1$ is a linear alkyl group of 3 or 5 carbon atoms, and $R^2$ is:

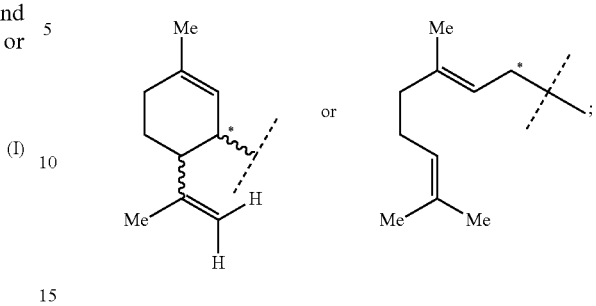

or of a pharmaceutical composition comprising the same.

An additional embodiment refers to a method for reducing solid tumor development, metastasis or chemo/radio-resistance, promoted by cancer stem cells, in a subject in need thereof, wherein said method comprises administering to said subject an effective amount of a compound of formula (I), or a pharmaceutically acceptable salt or solvate thereof:

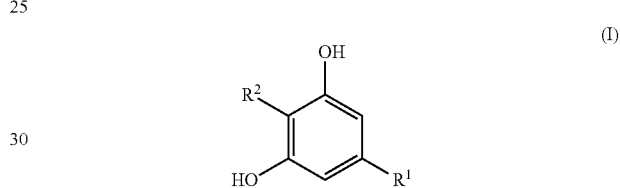
(I)

wherein $R^1$ is a linear alkyl group of 3 or 5 carbon atoms, and $R^2$ is:

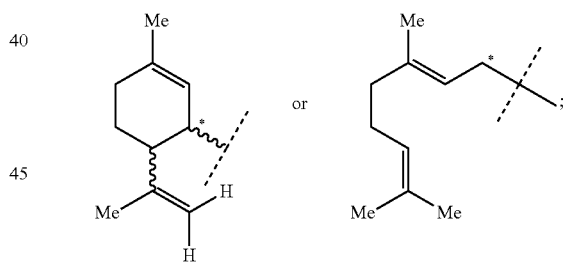

or of a pharmaceutical composition comprising the same.

One embodiment also refers to a method of treatment of a disease benefiting from Notch signaling pathway inhibition, i.e., a disease whose treatment benefits from Notch signaling pathway inhibition, and particularly the Notch1 signaling pathway. More specifically, present invention discloses a method of treatment of a disease whose treatment benefits from inhibiting or reducing Notch1 expression levels in cells, and/or benefits from inhibiting or reducing Notch1 levels in cells, and/or benefits from inhibiting or reducing Notch1 signaling dependent proteins levels in cells in a subject in need thereof, wherein said method comprises administering to said subject an effective amount of a compound of formula (I), or a pharmaceutically acceptable salt or solvate thereof:

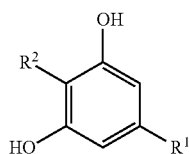

(I)

wherein R¹ is a linear alkyl group of 3 or 5 carbon atoms, and R² is:

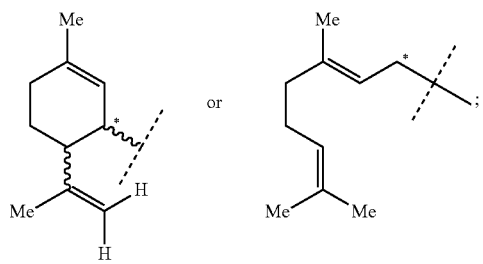

or of a pharmaceutical composition comprising the same. Preferably said Notch1 signaling proteins are transcription factors Hes1 and Hes5 For the purposes of present invention, an effective amount of the compound is that which provides either subjective relief of symptoms or an objectively identifiable improvement as noted by the clinician or other qualified observer.

The term "comprises" indicates that includes a group of certain features (for example a group of features A, B and C) is interpreted as meaning that it includes those features (A, B and C), but that it does not exclude the presence of other features (for example features D or E), as long as they do not render the claim unworkable. Additionally, the terms "contains", "includes", "has" or "encompass", and the plural forms thereof, should be taken as synonymous of the term "comprises" for the purposes of present invention. On the other hand, if the wording "consist of" is used, then no further features are present in the apparatus/method/product apart from the ones following said wording. In this sense, for the purposes of present invention, the term "comprises" may be replaced by any of the terms "consist of", or "consists essentially of". Accordingly, "comprises" may refer to a group of features A, B and C, which additionally may include other features, such as E and D, with the condition that said features do not render the claim unworkable, but said term "comprises" also includes the situation in which the group of features "consists of" or "consists essentially" of A, B and C.

The excipient included in the pharmaceutical compositions for use according to present invention, refers, for the purpose of present invention, to an inert ingredient such as, but not limited to, cosolvents, surfactants, oils, humectants, emollients, preservatives, stabilizers and antioxidants. Any pharmacologically acceptable buffer may be used, such as TRIS or any phosphate buffer.

In a preferred embodiment, the pharmaceutical composition for use according to present invention comprises cannabidiol (CBD), or a stereoisomer, or a mixture of stereoisomers thereof:

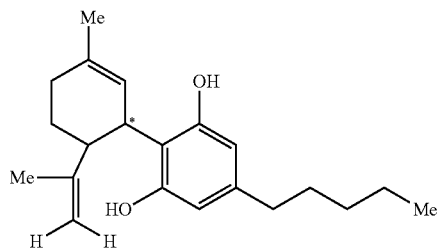

(CBD)

In another preferred embodiment, the pharmaceutical composition for use according to present invention comprises cannabidivarin (CBDV), or a stereoisomer, or a mixture of stereoisomers thereof:

(CBDV)

Additionally, in another preferred embodiment, the pharmaceutical composition for use according to present invention comprises cannabigerovarin (CBGV), or a stereoisomer, or a mixture of stereoisomers thereof:

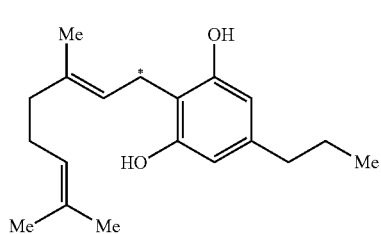

(CBGV)

In another preferred embodiment the pharmaceutical compositions for use according to present invention comprise at least one compound of formula (I), even more preferably at least one compound of formula (I) selected from the group consisting of cannabidiol (CBD), cannabidivarin (CBDV) and cannabigevarin (CBGV).

The compounds of formula (I) and pharmaceutical compositions comprising the same, disclosed in present invention may also be administered together, prior to, or subsequently to an additional therapy. Preferably said additional therapy is radiotherapy, immunotherapy or chemotherapy.

In a preferred embodiment, said pharmaceutical composition is administered together with, prior to or subsequently to a radiotherapeutic treatment, a chemotherapeutic treatment or an immunotherapeutic treatment In one embodiment, the pharmaceutical compositions disclosed comprise at least one additional active compound or therapeutic ingredient. Said additional active compound or therapeutic ingredient provides additive or synergistic biological activities. For the purposes of present description, the terms "active compound" or "therapeutic ingredient" should be taken as synonyms and mean a chemical or biological entity which exerts therapeutic effects when administered to human or animal beings. Said active compound or therapeutic ingredient exerts therapeutic effects when administered to human or animal beings, and it may be a cell therapy, a small molecule therapy, a immunotherapy, radiotherapy, among others. Preferably said active compound or therapy is a chemotherapeutic agent, a cell therapy or an immunotherapeutic agent.

In a preferred embodiment said additional active compound or therapeutic agent is selected from the group consisting of a CAR-T cell therapy, a CAR-NK cell therapy, a monoclonal antibody, a HIF pathway inhibitor and a chemotherapeutic agent. Said additional active compound or additional therapy may be administered at the same time, prior to, subsequently to, or at a different moment than the compound of formula (I) for use according to present invention. Preferably, said chemotherapeutic agent is selected from the group consisting of platinum-based antineoplastic agents, anti-mitotic chemotherapeutic agents, a poly adenosine diphosphate ribose polymerase (PARP) inhibitor, type I topoisomerase inhibitors, type II topoisomerase inhibitors, epothilones, cycloskeletal disruptors, alkylating agents, epothilones, histone deacetylase inhibitors, kinase inhibitors, antifolates, kinase inhibitors, peptide antibiotics, retinoids, *vinca* alkaloids and thymidylate synthase inhibitors. More preferably, the chemotherapeutic agent is selected from the group consisting of cyclophosphamide, ifosfamide, busulfan, temozolomide, mechlorethamine, chlorambucil, melphalan, dacarbazine, daunorubicin, doxorubicin, daunorubicin, epirubicin, idarubicin, mitoxantrone, valrubicin, paclitaxel, docetaxel, abraxane, taxotere, epothilone, vorinostat, romidepsin, irinotecan, topotecan, camptothecin, exatecan, lurtotecan, etoposide, teniposide, tafluposide, bortezomib, erlotinib, gefitinib, imatinib, vemurafenib, vismodegib, azacitadine, azathioprine, capecitabine, cytarabine, cladribine, fludarabine, doxifluridine, fluorouracil, gemcitabine, hydroxyurea, mercaptopurine, methotrexate, pemetrexed, tioguanine, bleomycin, actinomycin, carboplatin, cisplatin, oxaliplatin, tretinoin, alitretinoin, bexarotene, vinblastine, vincristine, vindesine and vinorelbine.

In another preferred embodiment said additional active ingredient is a HIF pathway inhibitor. Preferably said HIF pathway inhibitor is selected from apigenin, campothecin, topotecan, irinotecan, 2-methoxyestradiol, temsirolimus, echinomycin, romidepsin, geldanamycin, bortezomib, Vorinostat (SAHA), 2M2 NCD (panzem), 17-AAG (tanespimycin), 17-DMAG, PT2385, PT2977, EZN-2208, CRLX101 or any other compound inhibiting the HIF pathway.

In yet another preferred embodiment said additional active ingredient is a monoclonal antibody. Preferably said monoclonal antibody is selected mogamulizumab, blinatumomab, ibritumomab, obinutuzumab, ofatumumab, rituximab, tositumomab, inotuzumab, moxetumomab, brentuximab, gemtuzumab, daratumumab, isatuximab, alemtuzumab, polatuzumab, cetuximab, necitumumab, nimotuzumab, panitumumab, catumaxomab, burosumab, dinutuximab, pertuzumab, trastuzumab, ertumaxomab, mepolizumab, siltuximab, enfortumab, etaracizumab, racotumomab, bevacizumab, denosumab, elotuzumab, olaratumab, ramucirumab, bermekimab, labetuzumab, pemtumomab, tacatuzumab, pembrolizumab, nivolumab, cemiplimab, atezolizumab, avelumab, durvalumab, ipilimumab or any other immunotherapeutic agent.

Typical compositions include the compounds described above herein associated with pharmaceutically acceptable excipients, which may be a carrier or a diluent, as a way of example. Such compositions can be in the form of a capsule, sachet, paper or other container. In making the compositions, conventional techniques for the preparation of pharmaceutical compositions may be used. For example, the compounds disclosed above herein may be mixed with a carrier, or diluted by a carrier, or enclosed within a carrier that may be in the form of an ampoule, capsule, sachet, paper, or other container. When the carrier serves as a diluent, it may be solid, semi-solid, or liquid material that acts as a vehicle, excipient, or medium for the active compound. The compounds described above herein can be adsorbed on a granular solid container for example in a sachet. Some examples of suitable carriers are water, salt solutions, alcohols, polyethylene glycols, polyhydroxyethoxylated castor oil, peanut oil, olive oil, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent may include any sustained release material known in the art, such as glyceryl monostearate or glyceryl distearate, alone or mixed with a wax. Said compositions may also include wetting agents, emulsifying and suspending agents, preserving agents, sweetening agents or flavoring agents. The compositions of the invention may be formulated so as to provide quick, sustained, or delayed release of the compounds disclosed herein after administration to the patient by employing procedures well known in the art.

The pharmaceutical compositions can be sterilized and mixed, if desired, with auxiliary agents, emulsifiers, salt for influencing osmotic pressure, buffers and/or coloring substances and the like, which do not deleteriously react with the compounds disclosed above herein.

One preferred embodiment disclosed herein refers to the route of administration, that may be any route which effectively transports the compound disclosed above herein, to the appropriate or desired site of action, such as oral, nasal, topical, pulmonary, transdermal or parenteral, e.g., rectal, subcutaneous, intravenous, intraurethral, intramuscular, intranasal, ophthalmic solution or an ointment.

For nasal administration, the compositions may contain the compound disclosed above herein, dissolved or suspended in a liquid carrier, in particular an aqueous carrier, for aerosol application. The carrier may contain additives such as solubilizing agents, e.g., propylene glycol, surfactants, absorption enhancers such as lecithin (phosphatidylcholine), or cyclodextrin, or preservatives such as parabens.

To prepare topical compositions, the compound disclosed above herein, is placed in a dermatological vehicle as is known in the art. The amount of the compound disclosed above herein to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the compound disclosed above herein, and selects the amount of formulation administered, depending upon clinical experience with the patient in question or with similar patients.

For ophthalmic applications, the compound disclosed above herein, is formulated into solutions, suspensions, and ointments appropriate for use in the eye. The concentrations are usually as discussed above herein for local preparations.

For oral administration, either solid or fluid unit dosage forms can be prepared. For preparing solid compositions such as tablets, the compound disclosed above herein, is mixed into formulations with conventional ingredients such as talc, magnesium stearate, di-calcium phosphate, magnesium aluminum silicate, calcium sulfate, starch, lactose, acacia, methylcellulose, and functionally similar materials as pharmaceutical diluents or carriers.

Capsules are prepared by mixing the compound disclosed above herein with an inert pharmaceutical diluent and filling the mixture into a hard gelatin capsule of appropriate size. Soft gelatin capsules are prepared by machine encapsulation of slurry of the compound with an acceptable vegetable oil, light liquid petrolatum or other inert oil. Fluid unit dosage forms for oral administration such as syrups, elixirs and suspensions can be prepared. The water-soluble forms can be dissolved in an aqueous vehicle together with sugar, aromatic flavoring agents and preservatives to form syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanthin, methylcellulose and the like.

Appropriate compositions for parenteral use are apparent to the practitioner of ordinary skill, such as the use of suitable injectable solutions or suspensions. The composition, which is sterile, is suitable for various topical or parenteral routes including intra-dermal, intramuscular, intravascular, and subcutaneous.

In addition to the compounds disclosed above herein, the compositions may include, depending on the composition and mode of delivery desired, pharmaceutically-acceptable, non-toxic carriers or diluents, which include vehicles commonly used to form pharmaceutical compositions for animal or human administration. The diluents are selected so as not to unduly affect the biological activity of the combination.

Examples of such diluents that are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or non-toxic, non-therapeutic, non-immunogenic stabilizers and the like.

Furthermore, excipients can be included in the compositions disclosed. Examples include but are not limited to cosolvents, surfactants, oils, humectants, emollients, preservatives, stabilizers and antioxidants. Any pharmacologically acceptable buffer may be used, such as, tris or phosphate buffers. Effective amounts of diluents, additives, and excipients are those amounts that are effective to obtain a pharmaceutically acceptable formulation in terms of solubility, biological activity, etc.

The pharmaceutical compositions comprising the compound disclosed above herein may be incorporated into a microsphere. The compound disclosed above herein can be loaded into albumin microspheres, from which it is possible to recover such microspheres in a dry powder for nasal administration. Other materials suitable for the preparation of microspheres include agar, alginate, chitosan, starch, hydroxyethyl starch, albumin, agarose, dextran, hyaluronic acid, gelatin, collagen, and casein. The microspheres can be produced by various processes known to the person skilled in the art such as a spray drying process or an emulsification process.

For example, albumin microspheres can be prepared by adding rabbit serum albumin in phosphate buffer to olive oil with stirring to produce water in oil emulsion. Glutaraldehyde solution is then added to the emulsion and the emulsion stirred to cross-link the albumin. The microspheres can then be isolated by centrifugation, the oil removed, and the spheres washed, e.g., with petroleum ether followed by ethanol. Finally, the microspheres can be sieved and collected and dried by filtration.

Starch microspheres can be prepared by adding a warm aqueous starch solution, e.g. of potato starch, to a heated solution of polyethylene glycol in water with stirring to form an emulsion. When the two-phase system has formed (with the starch solution as the inner phase) the mixture is then cooled to room temperature under continued stirring whereupon the inner phase is converted into gel particles. These particles are then filtered off at room temperature and slurred in a solvent such as ethanol, after which the particles are again filtered off and laid to dry in air. The microspheres can be hardened by well-known cross-linking procedures such as heat treatment or by using chemical cross-linking agents. Suitable agents include dialdehydes, including glyoxal, malondialdehyde, succinicaldehyde, adipaldehyde, glutaraldehyde and phthalaldehyde, diketones such as butadione, epichlorohydrin, polyphosphate, and borate. Dialdehydes are used to cross-link proteins such as albumin by interaction with amino groups, and diketones form schiff bases with amino groups. Epichlorohydrin activates compounds with nucleophiles such as amino or hydroxyl to an epoxide derivative.

Another preferred embodiment of the invention is the dosage scheme of the compounds described above herein. The term "unit dosage form" refers to physically discrete units suitable as unitary dosages for subjects, e.g., mammalian subjects, e.g. humans, dogs, cats, and rodents, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the compound disclosed above herein and the particular effect to be achieved and (b) the limitations inherent in the art of compounding said compound for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described. The compositions disclosed herein can be included in kits, which can contain one or more-unit dosage forms of the composition and instructions for use to treat one or more of the diseases described herein.

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long-term source of therapeutic compound. Such slow release systems are applicable to formulations for delivery via topical, intraocular, oral, and parenteral routes.

The dosage of compounds used in accordance with the invention varies depending on the compound and the condition being treated for example the age, weight, and clinical condition of the recipient patient. Other factors include: the route of administration, the patient, the patient's medical history, the severity of the disease process, and the potency of the particular compound. The dose should be sufficient to ameliorate symptoms or signs of the disease treated without producing unacceptable toxicity to the patient.

Examples

The examples of the present invention described below aim to illustrate its preferred embodiments without limiting its scope of protection.

Example 1. CBD Impedes the In Vitro Formation of Colon Cancer Stem-Like Cells by Inhibiting Notch1 Signalling Pathway Cancer stem cells (CSC) cultured 3-dimentionally in a serum-free medium supplemented with growth factors are able to form floating spheroids known as tumorospheres (Reynolds B A et al. Dev Biol. 1996; 175(1):1-13. doi: 10.1006/dbio.1996.0090; Singh S K et al. Cancer Res. 2003; 63(18):5821-8. PMID: 14522905). These cancer cells-derived spheroids have been proven to display CSCs characteristics and recapitulate in vitro the in vivo conditions of cancer growth becoming an ideal model to evaluate anti-CSC drugs (Dieter S M et al. Cell Stem Cell. 2011; 9(4): 357-65. doi: 10.1016/j.stem.2011.08.010. PMID: 21982235; Lee C H et al. Oncotarget. 2016; 7(2):1215-26. doi: 10.18632/oncotarget.6261. PMID: 26527320). Human colorectal carcinoma HCT 116 cells cultured in that conditions form tumorospheres, known as colonospheres, which are enriched in CBC (complete blood count) markers and exhibit a complete CSC phenotype (Collura A et al. Cell Mol Life Sci. 2013; 70(4):729-42. doi: 10.1007/s00018-012-1160-9. PMID: 23007843; Huang R et al. Mol Med Rep. 2015; 12(2):2417-24. doi: 10.3892/mmr.2015.3694. PMID: 25936357; Shaheen S et al. Stem Cell Rev Rep. 2016; 12(4):492-9. doi: 10.1007/s12015-016-9664-6. PMID: 27207017).

Figure 1A:
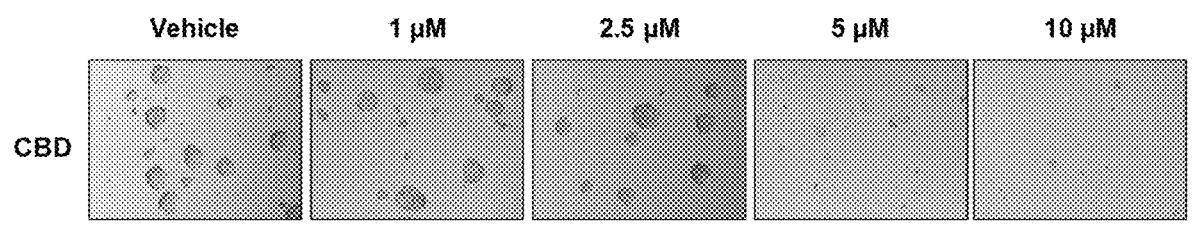
FIG. 1. The compound of formula (I), CBD, reduces colonospheres formation: (1A) Optical microscope images of colonospheres formed by HCT 116 cells (human colon cancer cell line) after 7 days of treatment with vehicle (DMSO) or with CBD (1, 2.5, 5 and 10 µM). (1B) Bar graph of the number of colonospheres formed by HCT 116 cells after 7 days of treatment with vehicle or with CBD (1, 2.5, 5 and 10 µM). Data are represented as mean±SEM (n=4 fields of views per condition). Statistical significance was determined by one-way ANOVA followed by Dunnett's post-hoc test. p<0.01; *p<0.001; ****p<0.0001 vs vehicle control cells.
Figure 1B:
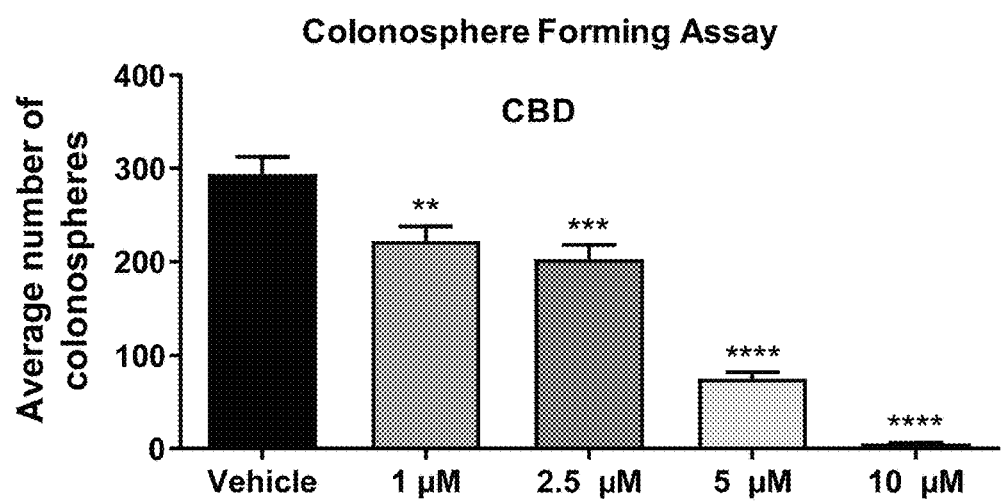

To study the CBD effect on colonospheres proliferation, a tumorospheres formation assay was performed. Briefly, human colorectal carcinoma HCT 116 cells (ATCC No. CCL-247) were trypsinized, quantified and seeded at clonal density (5 cell/µL) in ultra-low attachment surface 96-well plates (Corning-Costar. Coming, N.Y., USA) with serum free Dulbecco's Modified Eagle's Medium (DMEM)/Nutrient Mixture F-12 Ham (Sigma-Aldrich. St. Louis, Mo., USA) supplemented with 1X B-27 (Invitrogen, Carlsbad, Calif., USA), 10 ng/mL basic fibroblast growth factor (bFGF; PeproTech. London, UK), 20 ng/mL epidermal growth factor (EGF; Santa Cruz Biotechnology, Heidelberg, Germany), 1% (v/v) methylcellulose (R&D Systems. Minneapolis, Minn., USA) to prevent cell aggregation and the corresponding dose of vehicle (DMSO) or CBD concentration (1, 2.5, 5 and 10 µM). Every 2-3 days freshly supplements were added and the number and size of colonospheres were analysed by optical microscopy 1 week after seeding. Results from this assay showed that CBD treatment significantly reduces the colonospheres formation in a clear dose-dependent manner as shown FIGS. 1A and 1B.

In cancer stem cells Notch1 signalling pathway is abnormally activated (Venkatesh V et al. Stem Cell Investig. 2018 Mar. 12; 5:5. doi: 10.21037/sci.2018.02.02. PMID: 29682512). For this reason, to further analyse the antiproliferative CBD effect on colonospheres formation, Notch1 expression was investigated by western blot analysis. Briefly, after treatments, the colonospheres were washed with PBS1X and whole-cell proteins were extracted in 50 µL of lysis buffer (50 mM Tris-HCl pH 7.5, 150 mM NaCl, 10% glycerol and 1% NP-40) supplemented with 10 mM NaF, 1 mM Na3VO4, 10 µg/mL leupeptine, 1 µg/mL pepstatin and aprotinin, and 1 µL/mL phenylmethylsulfonyl fluoride saturated. Protein concentration of the whole-cell lysates was quantified by absorbance at 595 nm using Bradford reagent compared to a bovine serum albumin standard curve. Then, forty micrograms of protein were boiled at 95° C. in Laemmli buffer and electrophoresed in 10% SDS/PAGE gels. Separated proteins were transferred to polyvinylidene difluoride (PVDF) membranes (20V for 30 min) and blocked in TBSIX solution containing 0.1% Tween 20 and 5% non-fat dry milk for 1 hour at room temperature. Immunodetection of specific proteins was carried out by incubation with primary antibody against human Notch1 (1:1000 dilution. Ref. #ab52627, Abcam. Cambridge, UK) and β-actin (1:10.000 dilution. Ref. #A5316, Sigma-Aldrich. St. Louis, Mo., USA) overnight at 4° C. After washing membranes, horseradish peroxidase-conjugated secondary antibody was added and the protein bands on the membranes were detected with ECL reagent (BioRad. Hercules, Calif., USA) by chemiluminescence system (GE Healthcare Europe GmbH. Munich, Germany).

Figure 2A:
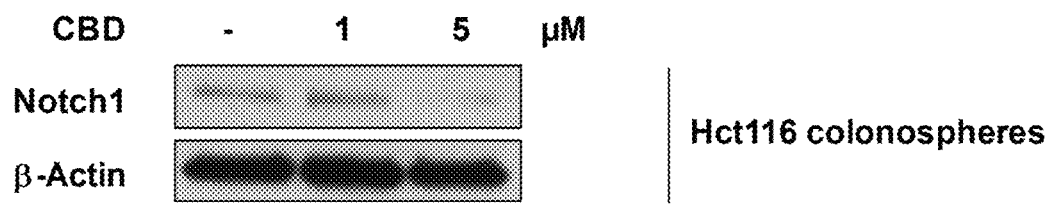
FIG. 2. The compound of formula (I), CBD, reduces Notch1 expression levels in colonospheres and HCT 116 cells: (2A) Notch1 expression levels in colonospheres after 7 days of treatment with vehicle (DMSO) or with CBD (1 and 5 µM). (2B) Notch1 expression levels in HCT 116 cells after 24 hours of treatment with vehicle (DMSO) or with CBD (1, 2.5, 5 and 10 µM). (2C) Notch1 expression levels at 6, 16 and 24 hours in HCT 116 cells treated with 10 µM CBD. Actin was used as control.

The densitometry analysis was performed using ImageJ software, and the quantified band intensities were normalized to Actin. In this assay, Notch1 levels were found to be clearly diminished in a dose-dependent manner in CBD-treated colonospheres compared with untreated cells, an effect that correlates with the described antiproliferative effect (FIG. 2A). Thus, it can be concluded that the reduction of Notch1 levels is critical to inhibit the colonospheres proliferation.

Example 2. CBD Induces Notch1 Degradation in Colorectal Cancer Cells

Figure 2B:
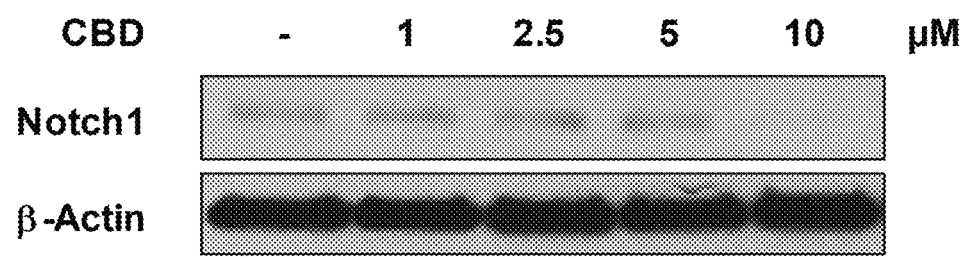
Figure 2C:
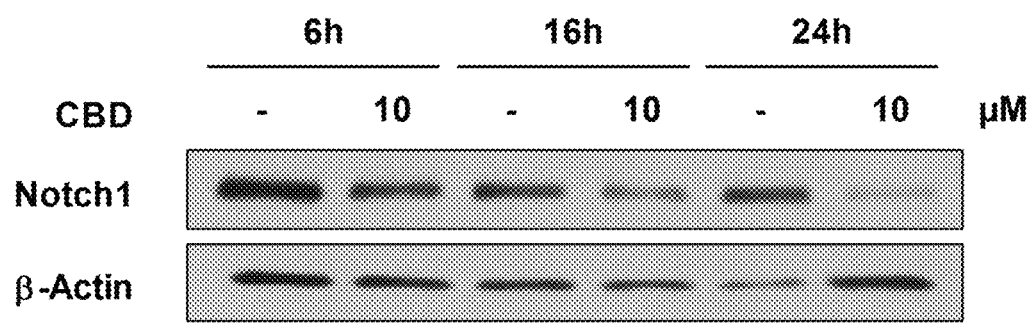
Figure 3A:
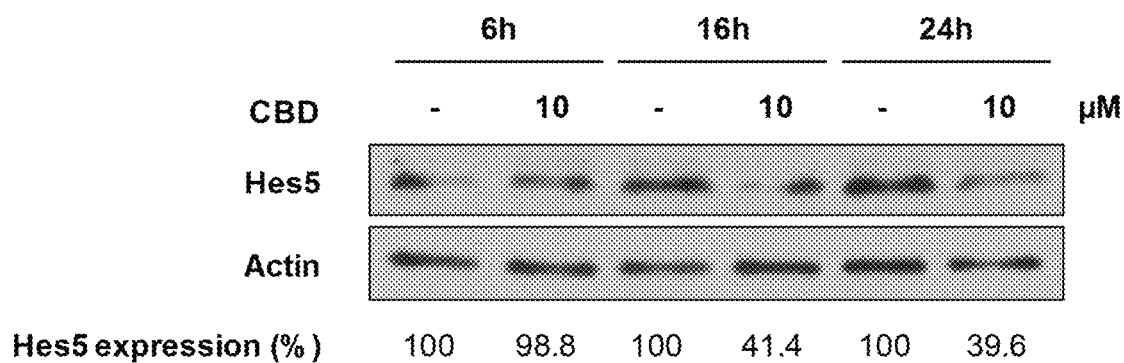
FIG. 3. The compound of formula (I), CBD, reduces the expression of Hes5 expression that is a Notch signalling-dependent protein, in HCT 116 cells: (3A) Hes5 expression levels at 6, 16 and 24 hours in HCT 116 cells treated with 10 µM CBD. Actin was used as control. (3D) Bar graph represents the quantification of the Hes5 expression levels by densitometry analysis. Densitometry analysis was performed using ImageJ software, and band intensities were normalized with regard to Actin.
Figure 3B:
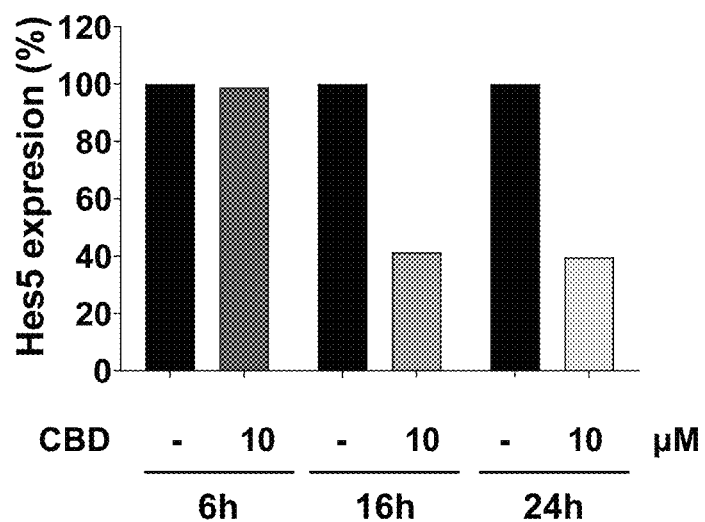
Figure 4:
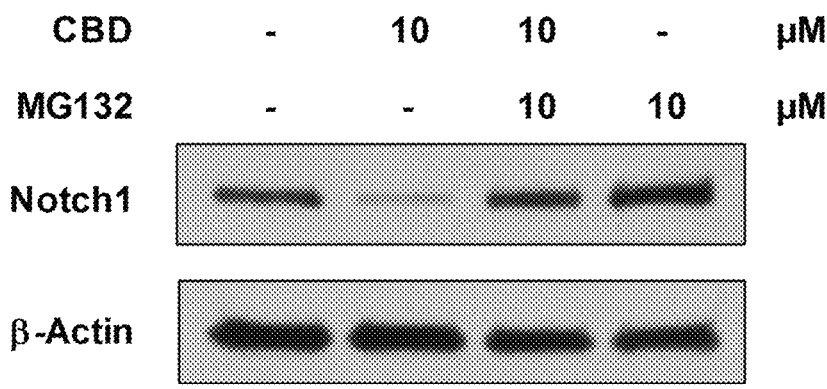
FIG. 4. The compound of formula (I), CBD, induces Notch1 degradation through the proteasome in colon cancer cells: Notch1 expression levels in HCT 116 cells after 24 hours of treatment with vehicle (DMSO) or with 10 µM CBD and/or 10 µM MG-132. Actin was used as control.
Figure 5A:
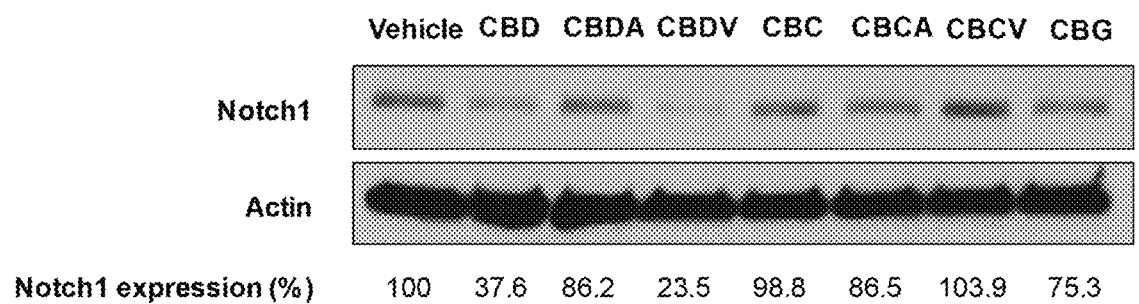
Figure 5B:
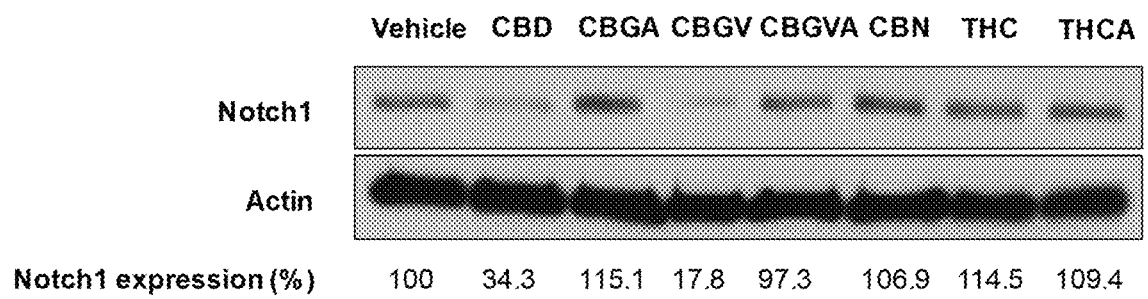
Figure 5C:
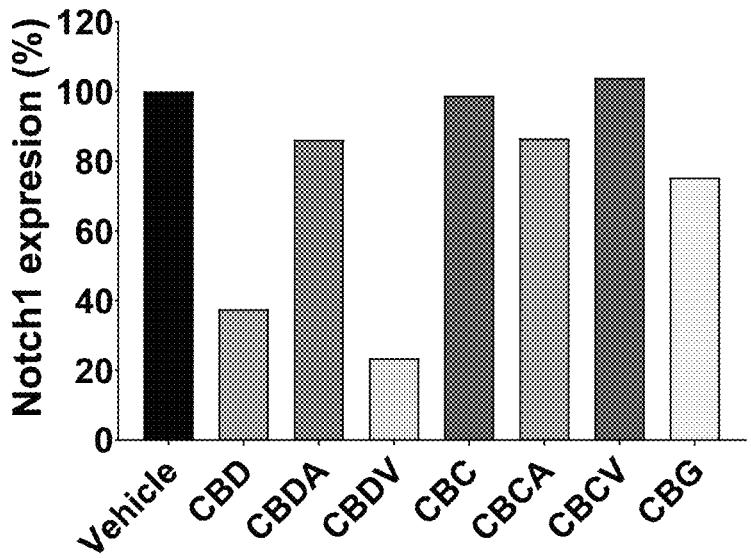
Figure 5D:
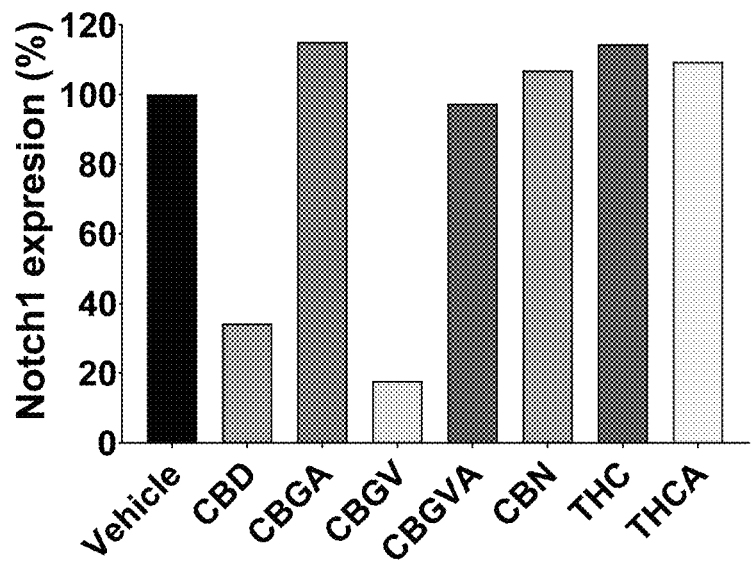

To gain insight into the CBD effect on Notch1 pathway, a deep study using the human colorectal carcinoma HCT 116 cell line (ATCC No. CCL-247) was performed to analyse Notch1 levels. Western blot analysis showed that CBD treatment reduces Notch1 protein levels in HCT 166 cells in a dose- and time-dependent manner (FIGS. 2B and 2C). Moreover, the Hes5 protein level, a Notch signalling-related protein, was also analysed by western blot following the methodology explained above and using a specific primary antibody (Human anti-Hes5. 1:1000 dilution. Ref. #ab25374, Abcam. Cambridge, UK). It is shown that CBD clearly reduces Hes5 expression levels in HCT 116 cells in a time-dependent manner (FIG. 3). To further clarify the CBD mechanism of causing a reduced Notch1 expression, HCT 116 cells were incubated with the proteasome inhibitor MG132 and/or with CBD. This assay demonstrated that CBD induces Notch1 degradation by the proteasomal degradation machinery in colon cancer cells (FIG. 4).

Example 3. CBDV and CBGV Reduce Notch1 Expression Levels in Colorectal Cancer Cells and Display an Anti-Proliferative Effect on Colon Cancer Stem-Like Cells A panel of natural cannabinoids CBDA, CBDV, CBC, CBCA, CBCV, CBG, CBGA, CBGV, CBGVA, CBN, THC and THCA were evaluated in its capacity to reduce Notch1 levels in human colorectal carcinoma HCT 116 cell line. CBD was purchase from Endoca BV (Netherlands). CBDA, CBDV, CBCA, CBG, CBGA, THC and THC were purchased from Phytoplant Research S.L (Cordoba, Spain).

CBC, CBCV, CBGV, CBGVA and CBN were provided by the laboratory of the Professor Giovanni Appendino from the University of Piemonte *Orientale* (Novara, Italy).

The results showed that among all tested natural cannabinoids only CBD, CBDV and CBGV clearly diminished Notch1 levels (FIGS. 5 and 6). Then, it was evaluated their effect on colonospheres formation. The experiment resulted that both natural varin cannabinoids, CBDV and CBGV, exert a potent dose-dependent anti-proliferative effect of colonospheres formation (FIGS. 7A and 7B).

Example 4. CBGV Exerts Inhibitory Effect on Notch1 Expression in Cancer Cells The effect of CBGV on Notch1 expression levels was evaluated in a panel of cancer cell lines. Human colorectal carcinoma Hct116 (No. CCL-247), human colorectal adenocarcinoma HT-29 (No. HTB-38), human brain neuroblastoma SK—N—SH (No. HTB-11), human breast adenocarcinoma MDA-MB-231 (No. HTB-26), human prostate adenocarcinoma PC3 (No. CRL-1435), human prostate carcinoma DU-145 (No. HTB-81), human lung carcinoma A549 (No. CCL-185) and human lung carcinoma H1299 (No. CRL-5803) cell lines were obtained from the American Type Culture Collection (ATCC, USA). This analysis showed the inhibitory effect of the CBVG on Notch1 expression in different cancer cell lines as shown in table 1:

Table 1 inhibitory effect of CBGV on Notch 1 levels
in different cancer lines

| Cell line | Inhibition of Notch1 expression in cancer cells CBGV |
|---|---|
| Hct116 (Colon) | Yes |
| HT-29 (Colon) | Yes |
| SK-N-SH (Brain) | Yes |
| MDA-MB-231 (Breast) | Yes |
| PC3 (Prostate) | Yes |
| DU145 (Prostate) | Yes |
| A549 (Lung) | Yes |
| H1299 (Lung) | Yes |

The invention claimed is:

1. A method of treating cancer in a subject in need thereof, said method comprising administering to said subject an effective amount of a compound selected from the group consisting of (−)-cannabidiol [(−)-CBD], (−)-cannabidivarin [(−)-CDBV], (+)-cannabidivarin [(+)-CBDV] and cannabigerovarin (CBGV):

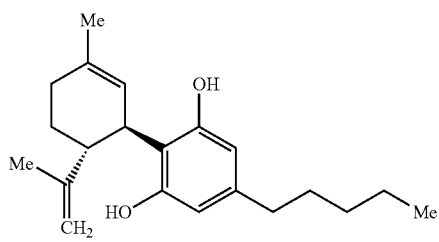

(-)-CBD

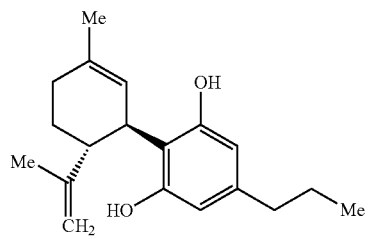

(-)-CDBV

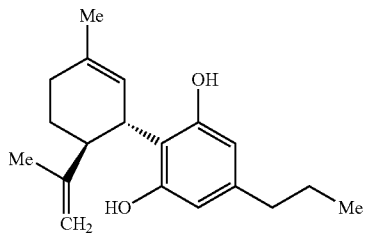

(+)-CDBV

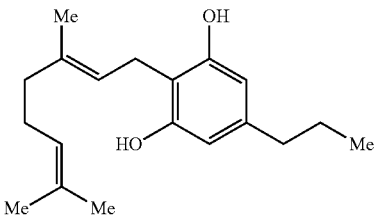

(CBGV)

wherein the cancer is a chemo- or radio-resistant tumor, wherein said chemo- or radio-resistant tumor is a cancer where a chemotherapeutic treatment or radiotherapy has not provided a remission of said cancer, and wherein said cancer is selected from the group consisting of: colon cancer, colorectal carcinoma, colorectal adenocarcinoma, prostate cancer, prostate adenocarcinoma, prostate carcinoma, breast cancer, breast carcinoma, breast adenocarcinoma, triple negative breast cancer, pancreatic cancer and glioma.

2. The method according to claim 1, wherein the cancer is selected from the group consisting of: colon cancer, colorectal carcinoma, colorectal adenocarcinoma, breast cancer, breast carcinoma, breast adenocarcinoma and triple negative breast cancer.

3. The method according to claim 1, wherein the cancer is selected from the group consisting of: colon cancer, colorectal carcinoma and colorectal adenocarcinoma.

4. A method of treating cancer in a subject in need thereof, said method comprising administering to said subject an effective amount of a pharmaceutical composition comprising at least one compound selected from the group consisting of (−)-cannabidiol [(−)-CBD], (−)-cannabidivarin [(−)-CDBV], (+)-cannabidivarin [(+)-CBDV] and cannabigerovarin (CBGV):

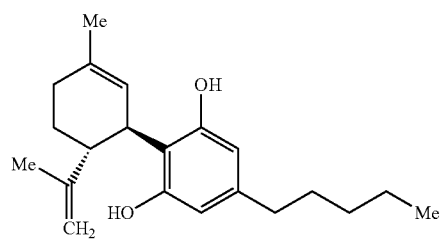

(-)-CBD

-continued

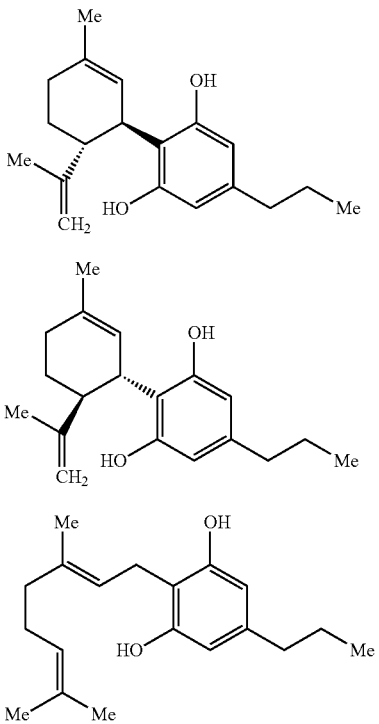

(-)-CDBV (+)-CDBV (CBGV)

and at least one pharmaceutically acceptable excipient, wherein the cancer is a chemo- or radio-resistant tumor, wherein said chemo- or radio-resistant tumor is a cancer where a chemotherapeutic treatment or radiotherapy has not provided a remission of said cancer, and wherein said cancer is selected from the group consisting of: colon cancer, colorectal carcinoma, colorectal adenocarcinoma, prostate cancer, prostate adenocarcinoma, prostate carcinoma, breast cancer, breast carcinoma, breast adenocarcinoma, triple negative breast cancer, pancreatic cancer and glioma.

5. The method according to claim 4, wherein the cancer is selected from the group consisting of: colon cancer, colorectal carcinoma, colorectal adenocarcinoma, breast cancer, breast carcinoma, breast adenocarcinoma and triple negative breast cancer.

6. The method according to claim 4, wherein the cancer is selected from the group consisting of: colon cancer, colorectal carcinoma and colorectal adenocarcinoma.

7. The method according to claim 4, wherein said pharmaceutical composition is administered together with, prior to, or subsequently to, a radiotherapeutic treatment, a chemotherapeutic treatment or an immunotherapeutic treatment.

8. The method according to claim 4, wherein the pharmaceutical composition further comprises at least one additional active compound or therapeutic ingredient.

9. The method according to claim 8, wherein said additional active compound or therapeutic ingredient is selected from the group consisting of: a CAR-T cell therapy, a CAR-NK cell therapy, a monoclonal antibody with anti-cancer activity, a HIF pathway inhibitor and a chemotherapeutic agent.

* * * * *